(12) United States Patent
Nelson et al.

(10) Patent No.: US 7,076,520 B2
(45) Date of Patent: Jul. 11, 2006

(54) COMPONENT ARCHITECTURE FOR MEDICAL DEVICE SYSTEM NETWORKS

(75) Inventors: Chester G. Nelson, Plymouth, MN (US); John B. Farr, St. Paul, MN (US); Kevin M. Johnson, St. Paul, MN (US); Charles R. Stomberg, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 906 days.

(21) Appl. No.: 09/844,658

(22) Filed: Apr. 27, 2001

(65) Prior Publication Data

US 2002/0032720 A1    Mar. 14, 2002

Related U.S. Application Data

(60) Provisional application No. 60/199,967, filed on Apr. 27, 2000.

(51) Int. Cl.
*G06F 15/16* (2006.01)

(52) U.S. Cl. ............... 709/203; 709/201; 709/202; 709/217; 709/221; 709/229

(58) Field of Classification Search ............... 709/203; 607/59, 30; 128/920
See application file for complete search history.

(56) References Cited

U.S. PATENT DOCUMENTS

| | | | |
|---|---|---|---|
| 4,809,697 A * | 3/1989 | Causey et al. | 607/31 |
| 5,161,222 A * | 11/1992 | Montejo et al. | 719/321 |
| 5,456,691 A * | 10/1995 | Snell | 607/30 |
| 5,759,199 A * | 6/1998 | Snell et al. | 607/60 |
| 5,800,473 A * | 9/1998 | Faisandier | 607/59 |
| 6,249,705 B1 * | 6/2001 | Snell | 607/59 |
| 6,250,309 B1 | 6/2001 | Krichen et al. | 128/899 |
| 6,565,609 B1 * | 5/2003 | Sorge et al. | 715/503 |
| 6,697,103 B1 * | 2/2004 | Fernandez et al. | 348/143 |

OTHER PUBLICATIONS

U.S. Appl. No. 09/426,741, filed on Oct. 26, 1999, entitled "Apparatus and Method for Remote Troubleshooting, Maintenance and Upgrade of Implantable Device Systems".
U.S. Appl. No. 09/430,708, filed Oct. 29, 1999, entitled "Tactile Feedback for Indicating Validity of Communication Link with an Implantable Medical Device".
U.S. Appl. No. 09/430,208, filed Oct. 29, 1999, entitled "Apparatus and Method for Automated Invoicing of Medical Device Systems".

(Continued)

*Primary Examiner*—Bunjob Jaroenchonwanit
*Assistant Examiner*—Dohm Chankong
(74) *Attorney, Agent, or Firm*—Daniel G. Chapik; Girma Wolde-Michael

(57) ABSTRACT

A component-based software architecture environment is provided for information networks used for administering one or more implantable medical devices (IMDs) in one or more patients. Various interface schema which may be used in implementing an IMD network are provided, as well as common interfaces for development of software within the network environment. The information network, and the software used in and implementing the network, may be upgraded and developed in a distributed and incremental manner, without requiring modification of entire systems or device instructions.

4 Claims, 4 Drawing Sheets

OTHER PUBLICATIONS

U.S. Appl. No. 09/431,881, filed Nov. 2, 1999, entitled "Method and Apparatus to Secure Data Transfer From Medical Device Systems".

U.S. Appl. No. 09/433,477, filed Nov. 4, 1999, entitled "Implantable Medical Device Programming Apparatus Having An Auxiliary Component Storage Compartment".

U.S. Appl. No. 09/731,178, filed Dec. 6, 2000, based on U.S. Appl. No. 60/173,071, filed Dec. 24, 1999, entitled "Automatic Voice and Data Recognition For Medical Device Instrument Systems".

U.S. Appl. No. 09/745,038, filed Dec. 20, 2000, based on U.S. Appl. No. 60/173,083, filed Dec. 24, 1999, entitled "Central Network to Facilitate Remote Collaboration With Medical Instruments".

U.S. Appl. No. 09/731,222, filed Dec. 6, 2000, based on U.S. Appl. No. 60/173,081, filed Dec. 24, 1999, entitled "Method and a System for Conducting Failure Mode Recovery in an Implanted Medical Device".

U.S. Appl. No. 09/750,739, filed Dec. 29, 2000, based on U.S. Appl. No. 60/173,822, filed Dec. 30, 1999, entitled "User Authentication In Medical Device Systems".

U.S. Appl. No. 09/775,281, filed Feb. 1, 2001, based on U.S. Appl. No. 60/180,289, filed Feb. 4, 2000, entitled "Responsive Manufacturing and Inventory Control".

U.S. Appl. No. 09/776,265, filed Feb. 2, 2001, based on U.S. Appl. No. 60/180,285, filed Feb. 4, 2000, entitled "Information Remote Monitor (IRM) Medical Device".

U.S. Appl. No. 09/732,951, filed Dec. 8, 2000, based on U.S. Appl. No. 60/184,221, filed Feb. 23, 2000, entitled "Follow-Up Monitoring Method and System For Implantable Medical Devices".

U.S. Appl. No. 09/797,031, filed Mar. 1, 2001, based on U.S. Appl. No. 60/186,235, filed Mar. 1, 2000, entitled "Implantable Medical Device With Multi-Vector Sensing Electrodes".

U.S. Appl. No. 09/799,304, filed Mar. 5, 2001, based on U.S. Appl. No. 60/187,280, filed Mar. 6, 2000, entitled "Stimulation For Delivery Of Molecular Therapy".

U.S. Appl. No. 09/809,483, filed Mar. 15, 2001, based on U.S. Appl. No. 60/189,562, filed Mar. 15, 2000, entitled "Individualized, Integrated, And Informative Internet Portal For Holistic Management of Patients With Implantable Medical Devices,".

U.S. Appl. No. 09/809,915, filed Mar. 16, 2001, based on U.S. Appl. No. 60/190,272, filed Mar. 17, 2000, entitled "Heart Failure Monitor Quick Look Summary For Patient Management Systems".

U.S. Appl. No. 09/437,615, filed Nov. 10, 1999, entitled "Remote Delivery Of Software-Based Training For Implantable Medical Device Systems".

U.S. Appl. No. 09/356,340, filed Jul. 19, 1999, entitled "Medical System Having Improved Telemetry".

U.S. Appl. No. 09/460,580, filed Dec. 14, 1999, entitled "Apparatus and Method for Remote Therapy and Diagnosis in Medical Devices Via Interface Systems".

U.S. Appl. No. 09/466,284, filed Dec. 17, 1999, entitled "Virtual Remote Monitor, Alert, Diagnostics and Programming For Implantable Medical Device Systems".

U.S. Appl. No. 09/474,694, filed Dec. 29, 1999, entitled "System Of Notification Of Recalled Components For A Medical Device".

U.S. Appl. No. 09/475,709, filed Dec. 30, 1999, entitled "A Communications System For An Implantable Device And A Drug Dispenser".

U.S. Appl. No. 09/745,112, filed Dec. 20, 2000, based on U.S. Appl. No. 60/172,937, filed Dec. 21, 1999, entitled "Instrumentation and Software for Remote Monitoring and Programming of Implantable Medical Devices (IMDs)".

U.S. Appl. No. 09/740,128, filed Dec. 20, 2000, based on U.S. Appl. No. 60/173,064, filed Dec. 24, 1999, entitled "Information Network Interrogation of an Implanted Device".

U.S. Appl. No. 09/746,230, filed Dec. 21, 2000, based on U.S. Appl. No. 60/173,065, filed Dec. 24, 1999, entitled "Medical Device GUI For Cardiac Electrophysiology Display And Data Communications".

U.S. Appl. No. 09/740,078, filed Dec. 18, 2000, based on U.S. Appl. No. 60/173,082, filed Dec. 24, 1999, entitled "Integrated Software System For Implantable Medical Device Installation And Management".

U.S. Appl. No. 09/745,143, filed Dec. 20, 2000, based on U.S. Appl. No. 60/173,083, filed Dec. 24, 1999, entitled "Dynamic Bandwidth Monitor And Adjuster For Remote Communications With A Medical Device".

U.S. Appl. No. 09/740,080, filed Dec. 18, 2000, based on U.S. Appl. No. 60/173,079, filed Dec. 24, 1999, entitled "Large-Scale Processing Loop For Implantable Medical Devices".

U.S. Appl. No. 09/740,127, filed Dec. 18, 2000, based on U.S. Appl. No. 60/173,062, filed Dec. 24, 1999, entitled "A Method and a System for Using Implanted Medical Device Data for Accessing Therapies".

U.S. Appl. No. 09/815,728, filed Mar. 26, 2001, based on U.S. Appl. No. 09/381,263, filed Sep. 17, 1999, which is baesd on US98/06085, filed Mar. 27, 1998, which is based on U.S. Appl. No. 60/042,367, filed Mar. 27, 1997, and also based on U.S. Appl. No. 60/192,006, filed Mar. 24, 2000, entitled "System and Method for Providing Remote Expert Communications and Video Capabilities for Use During a Medical Procedure".

U.S. Appl. No. 09/821,201, filed Mar. 29, 2001, based on U.S. Appl. No. 60/192,943, filed Mar. 29, 2000, entitled "A Hand-Held Surface ECG and RF Apparatus Incorporated With a Medical Device".

U.S. Appl. No. 09/821,518, filed Mar. 30, 2001, based on U.S. Appl. No. 60/193,881, filed Mar. 31, 2000, entitled "Variable Encryption Scheme For Data Transfer Between Medical Devices And Related Data Management Systems".

U.S. Appl. No. 09/825,909, filed Apr. 4, 2001, based on U.S. Appl. No. 60/194,512, filed Apr. 4, 2000, entitled "Implantable Medical Device Controlled By A Non-Invasive Physiological Data Measurement Device".

U.S. Appl. No. 09/696,319, filed Oct. 25, 2000, based on U.S. Appl. No. 60/197,753, filed Apr. 19, 2000, entitled "ECG and RF Apparatus For Medical Device Systems".

U.S. Appl. No. 09/838,697, filed Apr. 19, 2001, based on U.S. Appl. No. 60/198,974, filed Apr. 21, 2000, entitled "Passive Data Collection System From A Fleet Of Medical Instruments and Implantable Devices".

U.S. Appl. No. 60/198,973, filed Apr. 21, 2000, entitled "Report Configuration, Formatting and Distribution For Implantable Medical Devices And Instruments Network Systems", now abandoned.

U.S. Appl. No. 09/838,696, filed Apr. 19, 2001, based on U.S. Appl. No. 60/199,503, filed Apr. 25, 2000, entitled"Interface Devices For Instruments In Communication With Implantable Medical Devices".

U.S. Appl. No. 09/841,261, filed Apr. 24, 2001, based on U.S. Appl. No. 60/199,769, filed Apr. 26, 2000, entitled "GUI Coding for Identification of Displayable Data Quality From Medical Devices".

\* cited by examiner

COMPONENT ARCHITECTURE FOR MEDICAL DEVICE SYSTEM NETWORKS

CROSS-REFERENCE TO RELATED APPLICATIONS

This application claims the benefit of U.S. Provisional Application No. 60/199,967, filed Apr. 27, 2000.

FIELD OF THE INVENTION

The present invention generally relates to implantable medical devices and instruments. Specifically the invention relates to a system software architecture for medical device systems. More specifically, the invention pertains to implantable medical devices (IMDs) and instruments associated with them in a network environment, in which clinical and physiological data is transferred remotely, and a common software architecture is implemented to preferably develop and administer the network.

BACKGROUND OF THE INVENTION

The monitoring and administration of implantable medical devices (IMDs) may be well-suited to computerized and networked administration. The modern IMD is capable of sensing and storing large amounts of physiologic data from the host patient, and is also capable of implementing a treatment regimen based at least in part on this data—IMDs themselves naturally contain a powerful processing capacity in their own right. In addition, remote administration of IMDs via networks or other telecommunications media is being developed, and various IMD systems enable remote administration, such as those patient management and chronic systems as illustrated and described in applications assigned to the assignee of record entitled "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 10, 1999, Ser. No. 09/437,615; "Medical System Having Improved Telemetry," filed Jul. 19, 1999, Ser. No. 09/356, 340, now U.S. Pat. No. 6,298,271; "Apparatus and Method for Remote Therapy and Diagnosis in Medical Devices Via Interface Systems," filed Dec. 14, 1999, Ser. No. 09/460, 580; "Virtual Remote Monitor, Alert, Diagnostics and Programming For Implantable Medical Device Systems" filed Dec. 17, 1999, Ser. No. 09/466,284; "System Of Notification Of Recalled Components For A Medical Device" filed Dec. 29, 1999, Ser. No. 09/474,694; "A Communications System For An Implantable Device And A Drug Dispenser" Dec. 30, 1999, Ser. No. 09/475,709; "Instrumentation and Software for Remote Monitoring and Programming of Implantable Medical Devices (IMDs), filed Dec. 20, 2000, Ser. No. 09/745,112; "An Information Network Scheme For Interrogation Of Implantable Medical Devices (IMDs)," filed Dec. 18, 2000, Ser. No. 09/740,128; "Medical Device GUI For Cardiac Electrophysiology Display And Data Communications," filed Dec. 21, 2000, Ser. No. 09/746,230; "Integrated Software System For Implantable Medical Device Installation And Management," filed Dec. 18, 2000, Ser. No. 09/740,078; "Dynamic Bandwidth Monitor And Adjuster For Remote Communications With A Medical Device," filed Dec. 20, 2000, Ser. No. 09/745,143; "Large-Scale Processing Loop For Implantable Medical Devices (IMDs)," filed Dec. 18, 2000, Ser. No. 09/740,080; "A Method And System For Using Implanted Medical Device Data For Accessing Therapies," filed Dec. 18, 2000, Ser. No. 09/740,127; "Automatic Voice and Data Recognition For Medical Device Instrument Systems," filed Dec. 6, 2000, Ser. No. 09/731, 178; "Central Network to Facilitate Remote Collaboration With Medical Instruments," filed Dec. 20, 2000, Ser. No. 09/745,038; "Method And A System For Conducting Failure Mode Recovery In An Implanted Medical Device," filed Dec. 6,2000, Ser. No. 09/731,222; "User Authentication In Medical Systems Device," filed Dec. 29, 2000, Ser. No. 09/750,739; "Apparatus and Method For Automated Invoicing Of Medical Device Systems," filed Oct. 29, 1999, Ser. No. 60/173,824; "Responsive Manufacturing and Inventory Control," filed Feb. 1, 2001, Ser. No. 09/775,281; "Information Remote Monitor (IRM) Medical Device." filed Feb. 2, 2001, Ser. No. 09/776,265; "Follow-Up Monitoring Method And System For Implantable Medical Devices," filed Dec. 8, 2000, Ser. No. 09/732,951; "An Implantable Medical Device With Multi-Vector Sensing Electrodes," filed Mar. 1, 2001, Ser. No. 09/797,031; "Stimulator For Delivery Of Molecular Therapy," filed Mar. 5, 2001, Ser. No. 09/799,304; "Individualized, Integrated, And Informative Internet Portal For Holistic Management of Patients With Implantable Devices," filed Mar. 15, 2001, Ser. No. 09/809,983; "Heart Failure Monitor Quick Look Summary For Patient Management Systems," filed Mar. 16, 2001, Ser. No. 09/809,915; "A Universal Interface For Medical Device Data Management," filed Mar. 16, 2001, Ser. No. 09/809, 914; "System and Method For Providing Remote Expert Communications And Video Capabilities For Use During A Medical Procedure," filed Mar. 24,2000, Ser. No. 09/815, 728; "A Hand-Held Surface ECG and RF Apparatus incorporated With a Medical Device," filed Mar. 29, 2001, Ser. No. 09/821,201; "Variable Encryption Scheme For Data Transfer Between Medical Devices And Related Data Management Systems," filed Mar. 30, 2001, Ser. No,. 09/821, 518, "Implantable Medical Device Controlled ByA Non-Invasive Physiological Data Measurement Device," filed Apr. 4,2001, Ser. No. 09/825,909; "Method and Apparatus For Communicating With Medical Device Systems," filed Oct. 25, 2000, Ser. No. 09/696,319; "Passive Data Collection System From A Fleet Of Medical Instruments," filed Apr. 19, 2001, Ser. No. 09/838,697; "Report Configuration, Formatting and Distribution For Implantable Medical Devices And Instruments Network Systems," filed Apr. 21, 2000, Ser. No. 60/198,973, now abandoned; "Interface Devices For Instruments In Communication With Implantable Medical Devices," filed Apr. 19, 2001, Ser. No. 09/838, 696; "GUI Coding for Identification of Displayable Data Quality From Medical Devices," filed Apr. 24, 2001, Ser. No. 09/841,261; all of which applications are incorporated herein by reference in Their entirety. Networked and computerized IMD administration systems, based as they are on a distributed computerized environment pose numerous challenges in the development of software in the implementation or maintenance of such systems. The constituent processors of an IMD management system, for example, exist in numerous patients at the IMD level, and in an equally large number of residential and clinical settings, all of which are being modified, replaced, and upgraded at various times according to the needs of the patients and clinicians using the system at any given time. The administration of such a network is complicated further by the fact that the software implementing the network may be developed in a dispersed fashion—various IMDs, peripheral devices and monitoring equipment, and clinician and administrative computer environments may be developed in a way that is suitable for the task at hand, but may be without particular regard to other possible uses of the software, or the other network nodes with which the software must communicate. The resulting overall network may be implemented in an atomized, fragmented manner. In addition, the distributed nature of various IMD administration processes may limit the ability of remote users to effect the IMD-related function that is desired at the appropriate time. For example, a user desiring a physiological report regarding a patient may only be able to view such a report if they have direct access to an IMD programmer that has been programmed with The ability to generate reports.

Component-based software technology provides means for defining and using software components. Component technology, as implemented in evolving standards such as CORBA, DCOM and Enterprise Java Beans (EJB), provide the means for defining and using software components. The techniques of software component technology provide superior ways of developing and administering software.

Component technology is related to the developing object technology, which uses class-based software architecture to enable distributed and reusable programming. Under object technology, rather than a monolithic program, or even various software modules, software objects are provided with an interface which may be used by other programmers who may not be familiar with the internal workings of the software objects. Instead, they are provided with an interface which may take the form of certain defined datatypes, or of "public" functions, which they can access by providing known arguments or quantities, and they may expect a certain type of data according to the definition of the interface.

The interface may be implemented by means of datatypes meeting object or structure definitions both in the interface and the accessing program; the interface may also be accessed by means of "public" functions in the object of the interface. "Public" in this, the programming sense, means a function accessible to a later developer, but does not necessary imply that the interface definitions or functions will be published outside of the entity creating the interface code. The software objects may be encapsulated, i.e., it may be specified by the original author that they may not be modified by a programmer or developer who later uses the object. Just as the techniques of object oriented analysis, design and programming provide superior ways of dealing with the logical structure of software, so the techniques of component technology provide superior ways of dealing with the physical structure of software. A software component will ideally provide a well-defined, "guaranteed" interface which may be relied on by programmers; an implementation separated from the interface of which a programmer using the component may be ignorant; a physical implementation of the software that is separately releasable and versionable; and will be free from cyclic dependencies. This means that a component may not use, i.e. depend on another component, if that second component already depends directly or indirectly on the first component. These ideal characteristics of components provide for software that may have its functionality physically distributed among clients and servers across networks. The software may, in addition, have its functionality distributed across programming languages-providing interoperability between components implemented in different languages (C/C++, Java, Smalltalk, etc.).

An attendant benefit of this component architecture is that the software programming and maintenance task may be distributed—software may be divided into smaller pieces that can be built separately, but according to stable, common definitions assuring interoperability if the definitions are adhered to. This, in turn, provides more easily understood and maintained code. The cost of modifying the code is more easily estimated and controlled, should software changes be required. This in turn is due to the shortened incremental build times of components, because a change to the implementation of one component doesn't require rebuilding other components. The code is more easily reused by other projects, and standardized "off the shelf" development tools based on established components may be developed by various parties.

SUMMARY OF THE INVENTION

The present invention provides a component-based software architecture specifically adapted for enhancing the communication and operability of instruments and IMDs over a communications network. The invention may be implemented in a manner that is compatible with remote patient management systems that interact with remote data and expert data centers. Through use of the component-based software architecture environment, the information network and the software used in and implementing the network, may be upgraded and developed in a distributed and incremental manner, without requiring modification of entire systems or device instruction sets. Specifically, the invention is compatible with a data communication system that has the capacity to transfer clinical data from the patient to a remote location for evaluation, analysis, data reposition, and clinical evaluation. The component design of the software that may implement the present invention provides for distributing software functionality between network nodes without regard to the programming language or platform of the communicating components. The software functionality of the various components may, in addition to being distributed across nodes and languages, be distributed in time, i.e., the functions may take place at discrete and disparate times. The present invention may also be used with various data mining and network communication systems, including those implemented over a public network such as the Internet. According to one embodiment of the invention, component software architecture is implemented in conjunction with a hardware unit which provides functionality suited for the software architecture being implemented.

Modern IMD administration may be effected in large part through the use of interface instruments, i.e., dedicated IMD appliances that obtain data and instruct IMDs, and accordingly are capable of communication with deployed IMDs, for example, through telemetry. Examples of such interface instruments include, for example, IMD Programmers, IMD Extenders, IMD Interactive Remote Monitors, IMD Interface Medical Units, and IMD Pacing System Analyzers. The function of these devices, particularly in a networked environment, are detailed in the co-pending applications referenced above. According to a preferred embodiment of the present invention, code reuse may be implemented between these interface instruments, as well as within an interface instrument but across device applications. In other words, several software elements may be used in a single interface device, and be exploited in connection with several different IMDs or IMD functions. In this embodiment, software components may be developed that may have applicability to a number of different devices with which an instrument may interface.

In a further embodiment of the present invention, software developed according to the invention may be optimized for use on a standardized hardware module which may be incorporated into any interface instrument. This hardware module may be referred to generally as a Link Electronics Module, or LEM. The LEM may have the capacity to conduct telemetry communication with a deployed IMD, communicate with other IMD peripheral appliances such as Pacing System Analyzers, conduct IMD waveform and marker processing, conduct ECG waveform processing, and detect artifacts, i.e., the measurable effect of successful IMD functioning—the detection of the device administering therapy. Other functions preferably implemented in the LEM may include the consolidation or synchronization of data to facilitate or enable display, storage, and network transmission. Under this function, the LEM may poll various data sources, consolidate these sources into a message, e.g., an XML document, and transmit the data in a consolidated state. The LEM may also effect data compression or encryption, where the data payload is identified or standardized in accordance with defined component interface features. The LEM may also preferably consolidate or synchronize real-time data of various types or from various sources, e.g., ECG and EGM graphical data, together with applicable annotations to these graphical data, in the form of artifact and marker annotations. These data, which in their native format may arrive at different rates or times, as they are collected by different sensors and may be sampled at different rates; via the LEM they may be synchronized and/or consolidated, and presented per one or more component interfaces for transmission to various client routines; "client" in this context meaning a requesting process generally, and not necessarily a client network node. In addition, the LEM, through its software or firmware, may detect or implement state changes in the interface instrument or IMD, provide real-time or continuous recording of ECG samples and IMD waveform samples or markers, provide analog output of ECG or waveform samples, markers, or artifacts. This latter function, which may be considered a chart recording function, also preferably implements a report printing function which may be directly transmitted to a suitable display, plotter, or printer. The LEM may also be implemented to accept analog input from IMDs for processing by the LEM hardware unit or the interface instrument overall. Another common function required for interface instruments that may be implemented and standardized within the LEM is the upgrade or loading of executable or object code as firmware or software for execution on the interface instrument's master processor, which does not reside within the LEM. Similarly, the LEM may provide upgrades to the flash memory or similar instruction RAM of the IMD itself.

Peripheral software resident on interface instruments and other IMD peripheral devices may be implemented according to the invention to consist of two major parts: The first part is the peripheral subsystem running on the peripheral hardware or LEM. In order to incorporate the LEM into various interface instruments, a peripheral interface is developed for various interface instruments. The peripheral interface is implemented to run on that interface instrument's master processor, so that the functions of the LEM may be flawlessly incorporated into the functionality of the interface instrument as a whole. In this way, standardized LEM software components may be implemented and upgraded centrally using the component interfaces already accessed by the interface instrument processor.

Various common functions of interface instruments may be "componentized" according to the present invention. In a preferred embodiment, for example, a Report Generator component is developed that can execute within the Programmer or on other networked devices existing within a larger IMD administration network. This requires the device application, resident on the IMD itself, to export the required content in the agreed-upon format for the desired report. The user may then preferably be presented with the option to save the export image. In this way, the user may generate reports at a later time in a remote location if desired. This present invention also may execute a Waveform Monitor within a larger IMD administration network. In this way, saved waveform information, as opposed to real-time data, may be accessed via various remote computing and communication devices that have access to the IMD administration and support network. For example, a user at a remote PC may execute a waveform monitor device and be connected to an active programmer interfacing with the Peripheral Component. In this case the user would be able to view a live real time waveform from an implanted device. Based on the common component architecture of the system, upgrades to the PC or other device user interface or analytic software may be changed and upgraded without regard to the programming of the IMD itself, of the LEM, or of the interface instrument. Likewise, any of these components may themselves be reprogrammed without impact on the other elements, as long as the component interface definitions are respected. Other functions necessary for the functioning of an IMD administration network that may be implemented as component software modules within the LEM include the collection of real-time waveform data, e.g., ECG, EGM, and marker notation indicating when an IMD has administered a treatment or is in some other relevant operational status. In addition, the LEM with component software may process waveform data and perform analysis or the data or display the output of the ECG, for example. While an Implant Device Application may be changed, this will not have an impact on the LEM or any other network node, as long as the "public" component definitions are respected by the developers of the Implant Device Application.

DETAILED DESCRIPTION OF THE INVENTION

The present invention provides a component-based software architecture specifically adapted for enhancing the communication and interoperability of instruments and IMDs over a communications network, while providing a reusable and scalable software system that may be easily upgraded in a distributed fashion as new devices and functionalities are developed. The invention is preferably developed in a manner compatible with a communications network that implements a remote patient management systems that interact with remote data and expert data centers. At least some of the nodes of such a network are interface instruments, i.e., peripheral devices capable both of wireless communications with one or more IMDs in one or more patients, and of communications over a computer network. According to a preferred embodiment of the present invention, code reuse may be implemented between these interface instruments, as well as within an instrument but across device applications. In this embodiment, software components may be generated which may have applicability to a number of different devices that an instrument may interface with.

Figure 1:
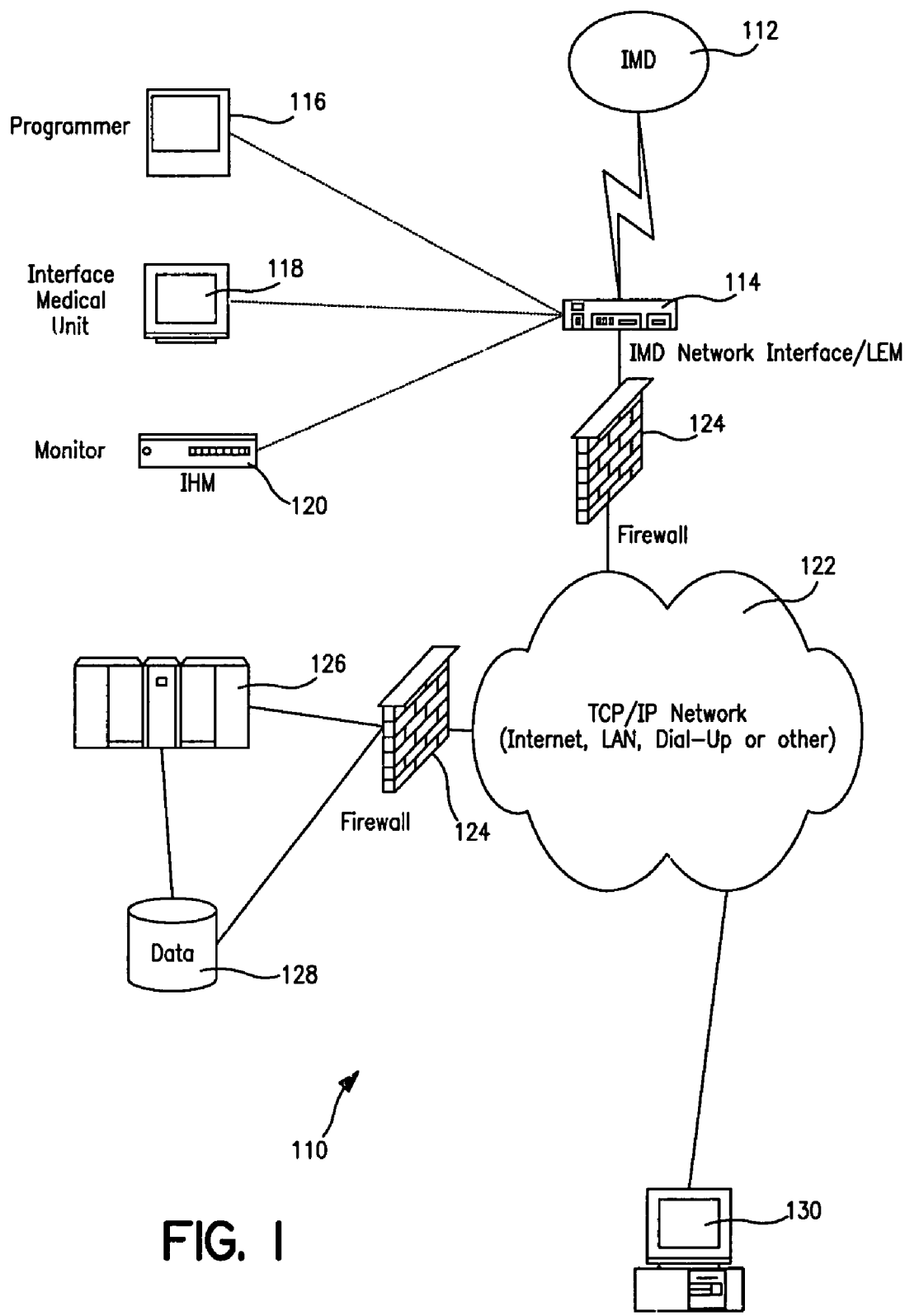
FIG. 1 is a schematic network diagram of an IMD administration network according to an embodiment of the present invention.

FIG. 1 depicts a typical IMD administration network 110 with which the present invention may be used, and as described in the related patent applications discussed above. IMD 112 is in telemetric communication with IMD network interface 114. IMD 112, representing one or more IMDs in one or more patients, may also or alternatively be in telemetric communication with programmer 116, interface medical unit 118, or remote monitor 120. Programmer 116, interface medical unit 118, and remote monitor 120 are examples of interface instruments as described generally herein. IMD network interface 114 may be replaced by, or may have installed within, a Link Electronics Module, or "LEM" unit, discussed below. Programmer 116, interface medical unit 118, or remote monitor 120 may also have within an LEM unit. The IMD network interface device 114, or interface instrument 116, 118, or 120, or the LEM installed within such instrument, is either directly, or via the LEM or IMD network interface device 114, in communication with network 122. Network 122 may be a public network, such as the Internet, if suitable security precautions are implemented such as firewalls 124. Through network 122 or other network connection, instrument 116, 118, or 120, directly or via internal LEM or IMD network interface 114, may communicate with centralized computing and monitoring computing resource 126. Computing resource 126 may have access to relevant database 128 relevant to administration of IMD 112. This network, and interface instruments 116, 118, and 120, may also be accessed by remote patient, clinician, or other authorized user personal computer 130.

Figure 2:
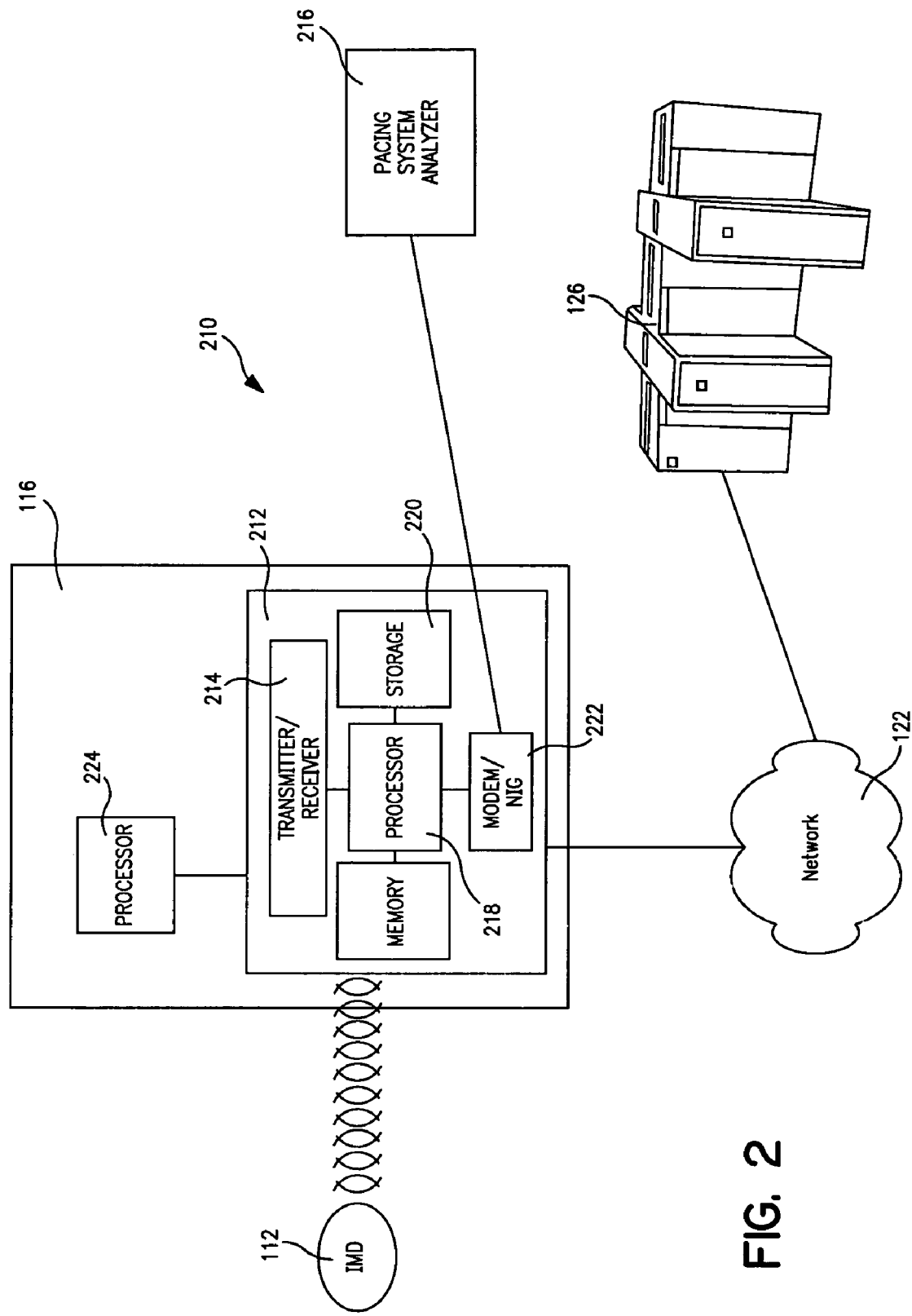
FIG. 2 is a schematic diagram showing the hardware environment in which an embodiment of the present invention may be implemented.

The positioning of a standardized hardware module, which may be termed a Link Electronics Module or LEM unit, which may be installed in interface instrument 114, 116, or 118 of FIG. 1, is depicted in FIG. 2 as a component of and relation to IMD network 210. Preferably, software developed according to the invention may be optimized for use on this standardized hardware module 212 which may then be incorporated into any interface instrument (e.g. 116, 118, or 120 of FIG. 1), providing component-based software functionality to the device. In a preferred embodiment, the LEM 212 will have the capacity to perform several typical functions common to various peripheral interface instruments regardless of the particular type of IMD 112 administered with the instrument. For example, the LEM 212 may be configured to conduct telemetry communication with a deployed IMD 112 via transmitter/receiver 214, communicate with other IMD peripheral appliances such as Pacing System Analyzers 216, conduct IMD waveform and marker processing via processor 218, conduct ECG waveform processing, and detect artifacts. Other functions preferably implemented in the LEM may include the synchronization of data to enable display, storage, and network transmission, all effected on processor 218. In addition, the LEM, through its component software or firmware stored in storage 220, may detect or implement state changes in the interface instrument or IMD 112, provide real-time or continuous recording of ECG samples and IMD waveform samples or markers, and provide analog output of ECG or waveform samples, markers, or artifacts. This latter function, which may be considered a chart-recording function, also preferably implements a report printing function which may be directly transmitted to a suitable display, plotter, or printer via modem or network interface module 222. The LEM may also be implemented to accept analog input from IMDs 112 or other physiological monitoring equipment for processing by the LEM device or the interface instrument 116 overall. Another common function required for interface instruments that may be implemented and standardized within the LEM 212 is the upgrade or loading of executable or object code as firmware or software for execution on the interface instrument's master processor 224, which does not reside within the LEM 212. Similarly, the LEM 212 may provide upgrades to the flash memory or similar instruction RAM of the IMD 112 itself. The primary function of the LEM with respect to the deployed IMD will be the downlinking of information requests, and the uplinking to the IMD administration network of the IMD's responses. The LEM 212 will have a similar information exchange relationship with Pacing System Analyzer 216, either via direct or networked communication, as depicted in FIG. 2, or via telemetry. LEM 212 will downlink information requests to the Pacing System Analyzer (PSA) 216, and uplink the responses of PSA 216, possibly after consolidating or integrating this data into waveform view information including ECG/EGM graphical information and annotations.

Certain LEM functions may be provided in hardware or firmware, in addition to flash memory, in order to improve the speed or efficiency of the LEM 212. These functions may be implemented in a manner complying with component definitions, so that the resulting LEM 212 may be easily implemented in most or all interface instruments without modification or translation or the device instructions. A software or firmware module implementing an interface with peripheral interface component will be required in order to make the LEM functions work with the particular interface instrument.

Figure 3:
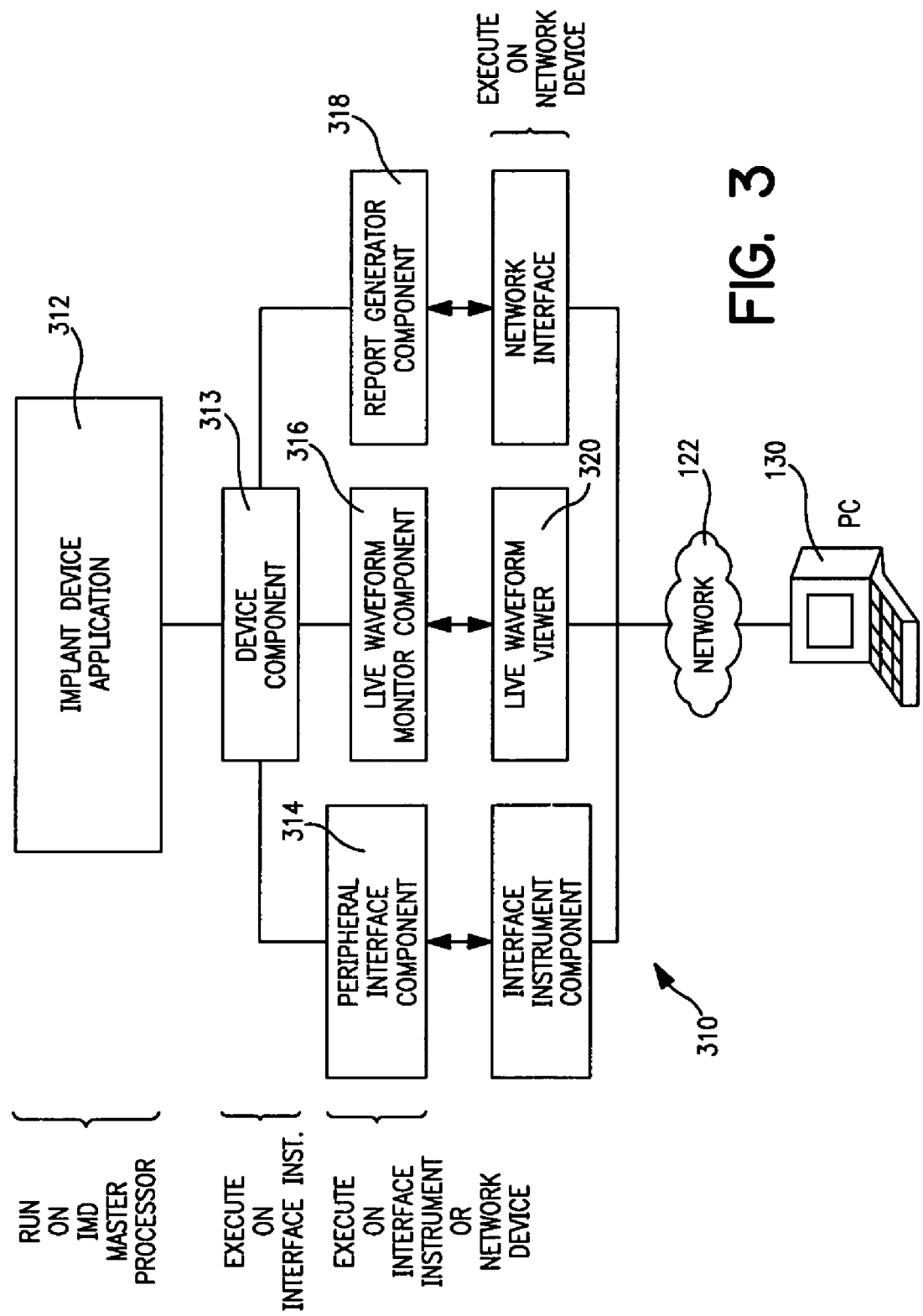
FIG. 3 is an architectural diagram for implementation of a software component system according to an embodiment of the present invention.

The software architecture afforded by the present invention is depicted in FIG. 3. A component software system for IMD administration networks is shown at 310. Implant device application 313 is resident within an implanted IMD, and executes on IMD master processor 224 of FIG. 2. Peripheral software components 314, 316 and 318 are resident on interface instruments such as 114, 116, and 118 of FIG. 1, and other IMD peripheral devices. These peripheral software components 314 may consist of at least two major parts; the first part being the peripheral subsystem running on the interface instrument hardware or LEM module within the interface instrument. In order to incorporate the LEM into various interface instruments, a peripheral interface 314 may be developed for various interface instruments. The peripheral interface may run on the master processor of the interface instrument, 224 of FIG. 2, or within LEM processor 218 of FIG. 2. In this manner, the functions of the LEM may be incorporated into the entire body of functionality of the interface instrument via interface compliant message passing between peripheral interface 314 running on interface instrument processor 224 of FIG. 2, and peripheral subsystem running on LEM 212 of FIG. 2. Standardized LEM software components may be implemented and upgraded centrally using the component interfaces already accessed by the interface instrument processor. LEM 212 may also provide for detection and reporting of relevant IMD state changes, many of which may be generalized across IMD types. LEM 212 may also flash or download executable code and configuration settings into storage of the remote interface instrument 116, 118 or 120 of FIG. 1.

The component system according to the invention may provide for reusable modules which perform various common functions of interface instruments. A major common function required of most interface instruments is report generation. A Report Generator component 318 may be developed that can execute within the IMD programmer 116 of FIG. 1, or other interface instrument 118 or 120, or within a larger IMD administration network, for example, on a remote machine 130 of FIG. 1. In this way, report generation is no longer confined to, nor must report generation be coded to, a particular medical support device. Data, preferably after being synchronized and compiled, may be sent to a Report Generator Component software module that may be resident within an IMD interface device, or within a network storage or processing device, and which may include, for example, remote personal computer 130 of FIG. 1. Generally, those components on the top interface tier of FIG. 3, i.e., Peripheral Interface Component 314, Live Waveform Monitor Component 316, and Report Generator Component 318, maybe resident or executed on an interface instrument such as programmer 116 of FIG. 1, or may be executed on a network device, including PC 130 of FIG. 1, of other suitable device within IMD information network 110. The networked device running, for example, the Live Waveform Monitor Component 316 may view static waveform information that has been stored, or may view a real-time waveform monitor session via an active programmer or other interface device properly interfacing to the Live Waveform Monitor Component 316.

The device application 312 will be resident on the IMD itself. In this embodiment, the device application must export the required content in the agreed-upon format for the desired report to Report Generator component 318. The user may then preferably be presented with the option to save the export image. In this way, the user may generate reports at a later time in a remote location such as personal computer 130 of FIG. 1 if desired. A component-based viewer may be provided in order to view the saved export image. This viewer necessarily uses the component framework of the system as a whole, particularly as regards graphic display.

The report generation component accepts implant session data or follow-up session data and generates the user selected report. Preferably, user customization will be provided. This customization may be implement locally, without impacting the operation of Report Generation Component 318. Only such information as the user has requested, and in the format requested, will be displayed to remote machine 130, according to component standardized requests for information, e.g., via message passing or function calls to public methods of the Report Generator Component 318, or via structured communications with Device Component 313, as discussed herein with reference to FIG. 4.

This present invention also may execute a Waveform Monitor Component 316 within a larger IMD administration network. In this way, saved waveform information, as opposed to real-time data, may be accessed via various remote computing and communication devices that have access to the IMD administration and support network. For example, a user at a remote PC 130 of FIG. 1 may execute a waveform monitor device via network interface 320, and be connected to an active programmer (e.g. 116 of FIG. 1) interfacing with the interface instrument. The live waveform monitor component 316 of FIG. 3 accepts real time or static waveform data and presents an integrated view to the user. The user can control the number of waveforms (combination of surface ECG and implant device EGM) along with markers and annotation information.

In this instance, the user would be able to view a live real-time waveform from an implanted device. Based on the common component architecture of the system, upgrades to the PC (130 of FIG. 1), or other device user interface or analytic software may be changed and upgraded without regard to the programming of the IMD 112 itself, of the LEM 212, or of the interface instrument. Likewise, any of these components may themselves be reprogrammed without impact on the other elements, as long as the component interface definitions are respected.

Figure 4:
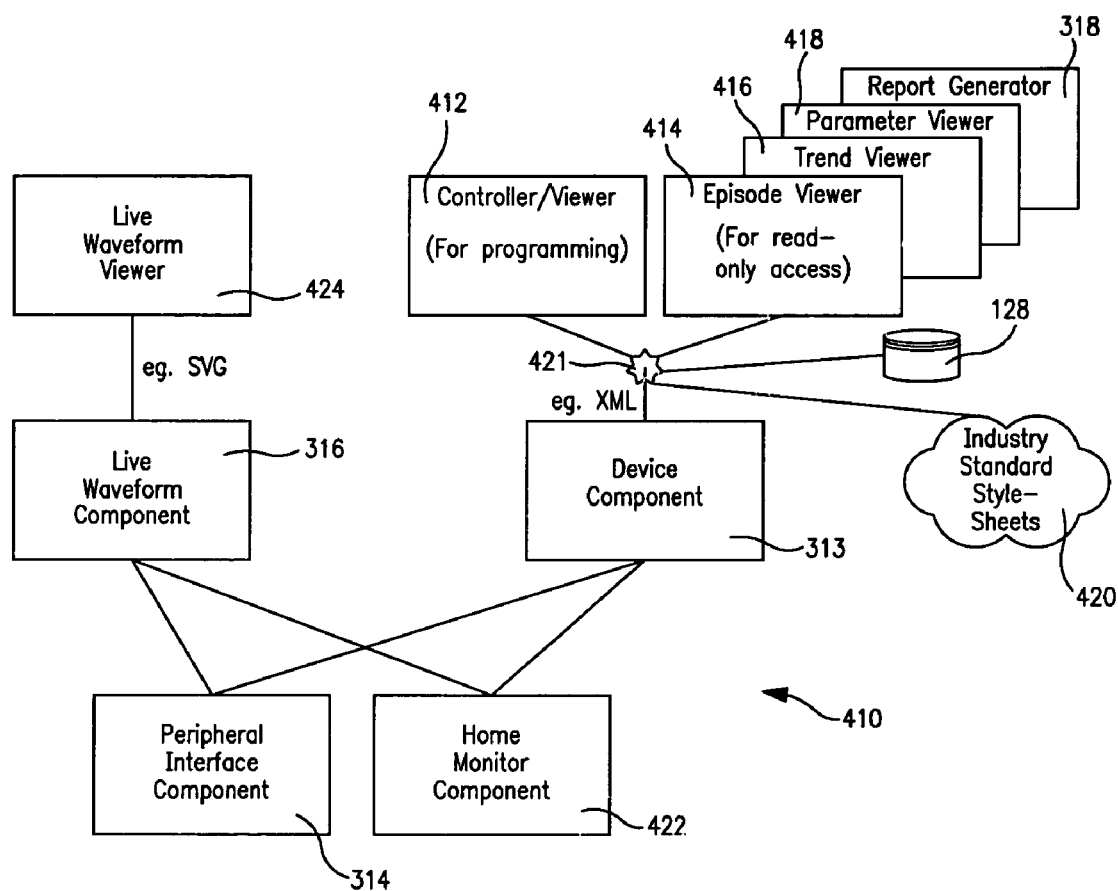
FIG. 4 is an architectural diagram of an alternative embodiment of a software component system according to the present invention.

An alternate software architecture embodiment of the present invention is depicted in FIG. 4. FIG. 4 depicts a Device component architecture generally at 410. Device Component 313 operates centrally within IMD (112 in FIG. 1) or interface instrument (114, 116, or 118 of FIG. 1). This component is encapsulated and protected from direct access by interface components discussed herein. The Device Component 313 may communicate via any number of structured communications schema, such as those suitable for client-server or other message passing, or function calls and returns. Suitable examples include CORBA, a JavaBeans API, DCOM, XSLT, OAP, or XML. This latter schema, XML, or eXtensible Markup Language, is expected to prove particularly suitable for non-analog interfacing of the components of the instant invention. As depicted in FIG. 4, Device Component 313 may send information and receive instructions from Controller/Viewer 412, which may be used for programming an IMD, or may interface via XML instructions and responses to Episode Viewer component 414, which may provide read-only access to IMD operation and physiologic information to individuals having properly authenticated access to a network having access to Device Component 313. Device Component 313 may also interface with Trend Viewer Component 416, Parameter Viewer 418, or Report Generator 318 , which may operate in a manner similar to Report Viewer Component 318 of FIG. 3. Device Component 313 may also interface via XML using a defined instruction and parameter dictionary with Database, e.g. of patient history information, or with Industry Standard Style-Sheets formatting component 420. The various potential interfaces to which Device Component 313 may interface via XML, this standard is depicted generally by virtual central interface 421.

Device Component 313 may also be accessed by properly authenticated individuals via Home Monitor Component 422 or Peripheral Interface Component 314. Peripheral Interface Component 314 may operate in a manner similar to that described with reference to FIG. 3. These interface communications may also be implemented using a structured, developer-defined, parsible communication schema such as XML. In a preferred embodiment of the present invention, real-time waveform data for a particular IMD may be accessed by a remote computer (e.g. 130 of FIG. 1), via Live Waveform Component 316. Live Waveform Component 316 may transmit data from Live Waveform Viewer Component 424 via a communication schema suitable for pictorial/image data, in order to transmit analog graphical information regarding the IMD functions and effect, in order to compare programmed treatment with actual treatment as indicated by interventional artifacts. A suitable scheme for transmission between components of this analog, or as transmitted what may be termed "pseudo-analog" pictorial representations, is Scalable Vector Graphics, or SVG, a mark-up language which is a W3C standardized grammar defined within the XML language. Such analog representations, when transmitted to Waveform Viewer Component 316, will preferably include useful data including IMD marker and artifact indications on the surface ECG/implant device EGM data, as well as other relevant annotation information. LEM 212 of FIG. 2 will also preferably accept analog or pseudo-analog input from other Components which may feed relevant information for processing by LEM 212. The components of FIG. 4, when implemented in accordance with the present invention as standardized interface components, may be individually developed, upgraded, replaced, and redesigned while respecting the interface definitions, such as those defined as XML tags, attributes, elements, or entities, collectively under an XML Document Type Definition suitable for transmission of IMD administration information.

While a preferred embodiment of the present invention has been described, it should be understood that various changes, adaptations and modifications may be made therein without departing from the spirit of the invention and the scope of the appended claims.

What is claimed is:

1. A computerized component architecture for medical device systems, comprising:
    a body of software components having standardized software interfaces to medical device interface instruments and implantable medical devices (IMDs); and
    at least one hardware module capable of executing the software components, with the at least one hardware module being deployable to multiple types of medical device interface instruments; said hardware module having means for communication with a data communications network, and with a medical device external to the hardware module, wherein said medical device interface instruments include the group consisting of: medical device programmers, medical device communication extenders, medical device system analyzers, and medical device monitors.

2. The computerized component architecture for medical device systems of claim 1, wherein at least one hardware module has processing and telemetry capabilities.

3. The computerized component architecture for medical device systems of claim 1, wherein at least one hardware module is installed within an interface instrument, to which it is deployable.

4. The computerized component architecture for medical device systems of claim 1, wherein the component software architecture is optimized to be executed on the hardware module.

* * * * *